United States Patent [19]

Zallie et al.

[11] Patent Number: 4,948,615
[45] Date of Patent: Aug. 14, 1990

[54] EXTRUDED GELLED PRODUCTS

[75] Inventors: James P. Zallie, Hillsborough; James J. Kasica, Whitehouse Station; James Eden, East Millstone, all of N.J.

[73] Assignee: National Starch and Chemical Investment Holding Corporation, Wilmington, Del.

[21] Appl. No.: 329,219

[22] Filed: Mar. 27, 1989

Related U.S. Application Data

[63] Continuation-in-part of Ser. No. 167,059, Mar. 11, 1988, abandoned.

[51] Int. Cl.$^5$ .......................................... A23L 1/0522
[52] U.S. Cl. ..................................... 426/578; 426/660; 426/658; 426/573
[58] Field of Search ................ 426/578, 579, 660, 658, 426/573

[56] References Cited

U.S. PATENT DOCUMENTS

| | | | |
|---|---|---|---|
| 3,265,508 | 8/1966 | Wurzberg et al. | 99/134 |
| 3,265,509 | 8/1966 | Wurzberg et al. | 99/134 |
| 3,265,510 | 8/1966 | Wurzberg et al. | 99/134 |
| 3,446,628 | 5/1969 | Schoch | 426/578 |
| 3,589,909 | 6/1971 | Godzicki et al. | 426/578 |
| 3,717,475 | 2/1973 | Germino | 426/578 |
| 4,219,582 | 8/1980 | Cheng | 426/578 |
| 4,225,627 | 9/1980 | Moore | 426/578 |
| 4,465,702 | 8/1984 | Eastman et al. | 426/578 |
| 4,567,055 | 1/1986 | Moore | 426/578 |
| 4,673,438 | 6/1987 | Wittwer et al. | 106/126 |
| 4,704,293 | 11/1987 | Moore | 426/578 |
| 4,726,957 | 2/1988 | LaCourse | 426/578 |

FOREIGN PATENT DOCUMENTS

36122122 4/1987 Australia .

*Primary Examiner*—Jeanette Hunter
*Attorney, Agent, or Firm*—Margaret B. Kelley; Edwin M. Szala

[57] ABSTRACT

A process for the extrusion of gelled products, such as jelly gum confectionaries, in a cooker of former extruder uses unique spray-dried pregelatinized high amylose starches alone or in blends with selected starches to provide extrudates which quickly set and form gels. The products typically contain about 10-18% of the starch (on a dry solids basis), about 70-90% of a sweetener, up to 20% water, and up to 20% of conventional confectionary or pharmaceutical ingredients. The mixture may be heated to about 93° C. (200°-240° F.) prior to extrusion to provide a flowable mixture. The spray-dried, pregelatinized high amylose starches (unmodified or modified) are prepared by a simultaneous steam atomization and spray-drying by process which provides a pregelatinized granular starch or a continuous coupled jet-cooking and spray-drying process which provides a pregelatinized dispersed starch which is substantially non-crystalline and substantially non-retrograded.

20 Claims, No Drawings

EXTRUDED GELLED PRODUCTS

This application is a continuation-in-part of Ser. No. 167,059, filed March 11, 1988, now abandoned.

BACKGROUND OF THE INVENTION

The present invention relates to the manufacture of gelled products such as jelly gum confectionaries and pharmaceutical products by extrusion, more particularly to extruded confectionaries and pharmaceutical products which include unique high amylose starches.

It has long been known that gum confections can be made with starch and, for many years, jelly bean centers and imitation fruit pieces, sometimes referred to as sugared jellies, have been made with ingredients including starch. These confectionaries have a firm gel structure. They are typically manufactured by a starch mold casting process, referred to in the trade as the Mogul system.

In this casting system, the ingredients, including a thin-boiling starch or a combination of a high amylose starch and a thin-boiling starch, are cooked at a moisture above the final moisture of the confectionary, and deposited as a thin, hot liquid into a mold generally formed of dry starch. The starch in the mold forms the confectionary pieces and serves to reduce the moisture content of the confectionary to the level of the end product. Typically, the cooked moisture level is about 15-30% in commercial continuous pressure cooking systems; the final moisture content is about 12-21%. This starch mold casting process has many disadvantages, particularly, the fact that the deposited candy pieces and molding starch must be dried for about 24-72 hours to reach the final product moisture content and a gel strength sufficient for handling and packaging.

An in-line extrusion process providing cooking and/or forming at the desired finished moisture content would be desirable. Most of the jelly gum confectionaries comprising jelly bean centers, imitation fruit pieces, and other snacks are presently made by the starch mold casting process. In order to get the desired gel structure, the starch has to be cooked at temperatures above the boiling point of the ingredients, i.e., above about 138.C. (280.F), and with moisture present in excess of that in the end product to achieve full gelatinization and a transparent to translucent gel. It is possible to cook at lower temperatures or with moisture starved conditions, but the starch does not fully dissolve and the ungelatinized starch essentially functions as a filler, with the consequence that the confectionary does not have the desired body, texture, and/or shelf life (i.e., the confectionary sweats which is due to inadequate gel structure).

Thus, it has been recognized that high temperature heating, well above the boiling temperature of the confectionary mixture, is required. In high temperature extrusion, one encounters problems with caramelization, air entrapment, and boiling and flash-off at the discharge orifice. The resultant textures range from that of hard candy to a tough licorice consistency. High temperature extrusion has not been successful in providing the classic resilient gel structure, clarity, and flavor attributes of the cast jelly gum confectionaries. Atmospheric cooking coupled with former extrusion (without heat) has not been successful in obtaining high quality gelled products due to poor set obtained from the starch when the candy is cooked under atmospheric conditions. Superatmospheric (i.e., steam injection) cooking, also referred to as jet-cooking, coupled with former extrusion (without heat) is also not commercially feasible due to the inability of the jet-cooker to handle very high viscosity finished solids confectionary formulations. High viscosity along with quick set are critical for the rope formation and handleability required for successful extrusion.

Various processes have been proposed for the manufacture of jelly gum confectionaries by extrusion.

U.S. Pat. Nos. 3,265,508 and 3,265,510 (issued Aug. 9, 1966 to O. B. Wurzburg et al.) describe extrusion processes. In the '508 patent the starch utilized is a converted starch containing no more than 35% amylose and having a fluidity above 20, e.g., dextrins and British gums. In the '510 patent the starch utilized is a native starch or a modified starch having a fluidity of less than 20. These thin-boiling starches do not provide a confectionary having the desired firm structure and transparent to translucent gel.

U.S. Pat. No. 3,265,509 (issued Aug. 9, 1966 to O. B. Wurzburg et al.) is also directed to an extrusion process. The starch utilized contains at least 50% amylose. High amylose starches typically require temperatures of at least about 149° C. (300° F.) even in dilute dispersions (below 50% solids) to gelatinize the starches. At the lower temperatures and higher solids levels used during extrusion (typically 80-86% solids), high amylose starches are not adequately gelatinized and largely function as fillers. At higher temperatures (about 204° C.-400° F.) the starches cook out but these conditions, which include an initial heating to about 82°-204° C. (180°-400° F.) and a die temperature in the range of about 32°-79° C. (90°-175° F.) and pressures ranging from about 50 to 5000 psi, are harsh, are difficult to obtain in most conventional extruders, and can lead to problems. The problems encountered include carmelization and off flavor development. Since heat-sensitive flavors have to be added prior to and/or during extrusion, it is important to be able to use mild extrusion conditions. As will be shown hereafter, it would be desirable to obtain a fast setting gel with a starch at milder extrusion conditions.

U.S. Pat. No. 4,567,055 (issued Jan. 28, 1986 to C. O. Moore) describes an extrusion process for the manufacture of jelly gum confectionaries wherein the starch utilized is an ungelatinized corn starch having a cold-water-solubility of greater than 25% which hydrates to be functional as a colloid. The cold-water soluble granular corn starches described in U.S. Pat. No. 4,465,702 (issued August 14, 1984 to J. E. Eastman) are suitable provided they have the required cold-water-solubility. As will be shown hereafter, the rapidity of gel formation resulting from this starch is not sufficient for the successful continuous extrusion of jelly gum confectionaries. In addition, jelly gum confectionaries made with this cold-water soluble corn starch have poor clarity.

Presently, jelly gum confectionaries are commercially manufactured by the casting process, which is a very lengthy process due mainly to the long time required for the confectionary to reach the required gel strength necessary for packaging. There is, therefore, a need for a process for preparing extruded jelly gum confectionaries which utilize starches that form firm gels quickly once cooked so that continuous extrusion can be successful.

Australian Patent Application P 36 12 212.2 describes injection molded or extruded pharmaceutical products prepared using a solvent-free N-vinylpyrrolid-2-one (NVP) polymer or copolymer as the fusible binder. Conventional extenders, such as silica or silicates, stearic acid or its salts, methylcellulose, talc, sucrose, lactose, cereal or corn starch, potato flour, or polyvinyl alcohol, can be used which include high amylose starches which entrap non-heat sensitive pharmaceutical compounds.

Presently, no extruded pharmaceutical products utilize starches to form a gelled matrix, contributing structure and encapsulating the active ingredients.

SUMMARY OF THE INVENTION

The present invention provides a process for the manufacture of a gelled product using a cooker extruder or a former extruder.

When a cooker extruder is used, the process comprises the steps of:

(a) mixing about 10 to 18%, on a dry solids basis, of a spray-dried, pregelatinized unmodified or modified high amylose starch (at least about 40% amylose) or a mixture of the spray-dried, pregelatinized high amylose starch and up to about 8 parts out of a total of 10 parts of a modified starch selected from the group consisting of a derivatized starch and/or a pregelatinized starch other than a high amylose starch, about 70 to 90% of a sweetener, and water present in a total amount of 0 to about 20%, the percentages being by weight and totaling 100%; characterized in that the spray-dried, pregelatinized high amylose starch comprises (i) a modified or unmodified, uniformly gelatinized granular starch in the form of indented spheres, with at least a majority of the granules being whole and unbroken, the starch granules being in the form of loosely-bound agglomerates or individual granules, (ii) a modified or unmodified, fully dispersed, non-granular starch which is substantially non-crystalline and substantially non-retrograded, or (iii) mixtures thereof;

(b) heating the mixture to about 93° C. (200° F.) to provide a flowable mixture;

(c) introducing the hot mixture into a cooker extruder and heating at about 93°–149° C. (200°–300° F.) for a time sufficient to fully disperse the starch or the starch mixture; and (d) extruding the mixture as a firm gel.

When a former extruder is used, the process comprises the steps of:

(a) mixing about 10 to 18%, on a dry solids basis, of a spray-dried, pregelatinized unmodified or modified high amylose starch (at least about 40% amylose) or a mixture of the spray-dried, pregelatinized high amylose starch and up to about 8 parts out of a total of 10 parts of a starch other than the high amylose starch selected from the group consisting of a granular starch, converted starch, derivatized starch, and/or pregelatinized starch, about 70 to 90% of a sweetener, and water present in a total amount of 0 to about 20%, the percentages being by weight and totaling 100%; characterized in that the spray-dried, pregelatinized high amylose starch comprises (i) a modified or unmodified, uniformly gelatinized granular starch in the form of indented spheres, with at least a majority of the granules being whole and unbroken, the starch granules being in the form of loosely-bound agglomerates or individual granules, (ii) a modified or unmodified, fully dispersed, non-granular starch which is substantially non-crystalline and substantially non-retrograded, or (iii) mixtures thereof;

(b) heating the mixture to about 93°–116° C. (200°–240° F.) for a time sufficient to fully solubilize the sugar and starch or the starch mixture and to increase the solids to about 80–86%;

(c) introducing the hot mixture into a former extruder; and (d) extruding the mixture as a firm gel.

Speed of set is critical for both cooker extrusion and former extrusion since the extrudate will be immediately cut and cut while hot when the product exits the extruders. As will be shown in the Examples, a high gel strength when the extrudate is cold is not necessarily related to the quick set required for handleability. Gel strength as shown by quick set at time of extrusion is the most critical requirement for successful extrusion. This is measured as handleability and rope formation.

Up to about 10%, preferably 5%, of a pharmaceutically active compound is included in the mixture of step (a) when a pharmaceutical product is being prepared. If desired, the pharmaceutical product may be provided with a conventional coating to improve the appearance or to delay release of the active compound.

Optional ingredients can include up to about 20% of a confectionary ingredient selected from the group consisting of a flavorant, colorant, fat, oil, surfactant, humectant, vitamin, preservative and mixtures thereof or up to 20% of a conventional pharmaceutical auxiliary selected from the group consisting of a flavorant, colorant,, acid, preservative, and mixtures thereof. The optional ingredients can be included in the mixture of step (a).

DETAILED DISCLOSURE OF THE INVENTION

The present invention is directed to the manufacture by extrusion of gelled products such as jelly gum confectionaries and pharmaceutical products. A mixture of a unique spray dried, pregelatinized high amylose starch and sugar is used in the extruded product. The extruded product has a firm gel structure.

Such confectionaries do not include hard candy; neither do they include gels with flowable characteristics. The end confectionary products are of three basic types which vary primarily in gel texture and coating procedure.

The jelly gum confectionary may be moistened with steam and rolled in granulated sugar to produce the classic gum drop, fruit slice or bar, or similar pieces ("sugared jellies"). The gels in these confections are firm and have ample resiliency for shape retention when marketed in stacked bags or in bulk. However, the eating qualities of the gel are desirably a soft tender bite and moderately quick dissolving when chewed. A second type of gel confection is jubes or hard gums produced from the same primary gel ingredients as sugared jellies, but lower in moisture content and generally containing additional starch. The surface is coated with an edible oil, rather than granulated sugar. By intent, the finished confection is much firmer in gel strength, characteristically tougher to bite, and longer lasting when chewed, than sugared jellies. A third type of gel confection is jelly beans having starch jelly centers which are resilient and firm enough for tumbling in a revolving pan for coating with a sugar shell. All of these confections have in common, firm, resilient gel structure.

Since the gelled products will be extruded, the ingredients making up the confectionary or pharmaceutical product will be mixed together in the proportions which occur in the resulting product and at the moisture level equivalent to that resulting after extrusion. The mixed ingredients should be fluid so as to be readily introduced into the extruder without the incorporation of air. The ingredients will include the unique spray-dried pregelatinized high amylose starches or starch blends, to be described hereinafter, at a total starch level of between about 10 and about 18%, on a dry solids basis, preferably between 11 and 16%. When a starch blend is used, the total solids will typically be only about 11% due to viscosity restrictions. At least 2 parts (out of a total of 10 parts), preferably 4 parts, of the blend must be the high amylose starch. Sweeteners are used at a level of between about 70 and 90%, on a dry solids basis. When a pharmaceutical product is being prepared, an effective amount of the pharmaceutically active ingredient will be included, typically about 5%, on a dry solids basis. Optional ingredients in an amount of up to about 20%, on a dry solids basis, may be added.

The particular spray-dried, pregelatinized high amylose starches useful herein are a significant feature of the invention. The modified or unmodified starches are cooked and spray-dried under conditions which provide pregelatinized starches with unique properties. The applicable starch bases which may be employed may be derived from any high amylose plant source which contains concentrations of about 40–100% amylose, including, for example, high amylose corn and wrinkled pea. The preferred starches are those derived from high amylose corn hybrids. Unmodified starches are preferred; however, modified starches such as converted starches (also referred to as fluidity starches) and/or derivatized starches are also useful herein. Such modifications are conventional in the art and described hereafter.

A method for preparing suitable spray-dried, pregelatinized starches is described in U.S. Pat. No. 4,280,851 (issued July 28, 1981 to E. Pitchon et al.). In this process a mixture of the granular starch is cooked or gelatinized in an atomized state. The starch which is to be cooked is injected through an atomization aperture in a nozzle assembly to form a relatively finely-divided spray. A heating medium is also injected through an aperture in the nozzle assembly into the spray of atomized material so as to heat the starch to a temperature effective to gelatinize the starch. An enclosed chamber surrounds the atomization and heating medium injection apertures and defines a vent aperture positioned to enable the heated spray of starch to exit the chamber. The arrangement is such that the elapsed time between passage of the spray of starch through the chamber, i.e., from the atomization aperture and through the vent aperture defines the gelatinization time of the starch. The resulting spray-dried, pregelatinized starch comprises uniformly gelatinized starch granules in the form of indented spheres, with a majority of the granules being whole and unbroken and swelling upon rehydration. Nozzles suitable for use in the preparation of these starches are also described in U.S. Pat. No. 4,610,760 (issued Sept. 9, 1986 to P. A. Kirkpatrick et al.)

Spray-dried, pregelatinized high amylose starches with suitable properties can be provided by the continuous coupled jet-cooking and spray-drying process described in our copending application Ser. No. 242,657 filed Sept. 12, 1988. The starch is cooked at a solids and temperature sufficient to substantially reduce its viscosity. Typically, a starch slurry (up to 38% anhydrous) is mixed and gelatinized at 138°–160° C. (280°–320° F.) with high-temperature steam (at 140°–160 psi) in a continuous direct steam injection jet-cooker. The starch slurry and steam streams are mixed in a cooking chamber. The exit of the cooking chamber is connected to a pneumatic-type spray-nozzle or high pressure single fluid nozzle situated in a conventional spray-drier. The jet-cooked starch (still under elevated temperature and pressure) is directed into the spray-nozzle and atomized with cold air, hot air, or preferably steam into a preheated air flow. Once the hot jet-cooked starch solution has been atomized, it is handled in the same manner as conventional spray-dried starches. The drying process is sufficiently rapid to prevent retrogradation of the starch molecules as the droplets cool and dry. The spray-dried starch is an amorphous solid (i.e., substantially non-crystalline) and is readily water-soluble.

Either of these unique pregelatinized, spray-dried high amylose starches may be used alone, in combination, or in blend with starches other than high amylose starches which are selected from the group consisting of selected derivatized starches and/or pregelatinized starches, provided the high amylose starch is present in an amount of at least 20% by weight on a dry solids basis in the blend.

converted starches, also referred to as fluidity or thin-boiling starches, are starches whose molecular weight has been reduced by mild acid hydrolysis or enzyme conversion. Such starches are not useful in a cooker extruder unless they have been pregelatinized. For example, an acid-converted corn starch having a water fluidity of about 65 W.F. will not disperse at the high solids level used in the mixture, whereas a pregelatinized acid-converted starch will disperse. Such starches are useful in a former extruder provided the starches have been fully dispersed prior to introducing the mixture into the former extruder. For the preparation of converted starches, acid or enzyme conversion can be used.

In preparation of the converted starches by acid treatment, the granular starch base is hydrolyzed in the presence of an acid, such as sulfuric or hydrochloric acid, at a temperature below the gelatinization point of the starch. The starch is slurried in water, and the acid (usually in concentrated form) is then added. Typically, the reaction takes place over an 8–16 hour period, after which the acid is neutralized with alkali (e.g., the pH of 5.5), and the starch recovered by filtration.

In the preparation of the converted starches by enzyme treatment, the granular starch base is slurried in water, and the pH is adjusted to about 5.6–5.7 with alkali or acid. A small amount of alpha amylase enzyme (e.g., about 0.02% on the starch) is added to the slurry which is then heated above the gelatinization point of the starch. When the desired conversion is reached, the pH is adjusted with acid (e.g., to about 2.0) to deactivate the enzyme and the dispersion is held at the pH for a period of at least 10 minutes. Thereafter, the pH may be readjusted. The resulting converted starch dispersion is then usually recovered by spray-drying.

Derivatized starches, as well as converted and derivatized starches, are suitable for use in the cooker extruder provided the starch disperses during the extrusion and for use in a former extruder provided the starch is fully dispersed prior to introduction of the mixture into the former extruder. Suitable derivatives must have a low gelatinization temperature. The derivatives can include esters such as the acetate and half-esters such as the succinate and octenylsuccinate prepared by reaction with acetic anhydride, succinic anhydride and octenylsuccinic anhydride, respectively; the phosphate derivative prepared by reaction with sodium or potassium orthophosphate or tripolyphosphate; ethers such as hydroxypropyl ether prepared by reaction with propylene oxide; and any other edible starch derivatives having a low gelatinization temperature and approved for use in food products.

Derivatized and crosslinked starches can be used provided the balance between stabilization and crosslinking permits the modified starch to disperse during extrusion or prior to extrusion. For example, a mixture containing a crosslinked and hydroxypropylated waxy maize starch (9% propylene oxide) was extruded in a cooker extruder and no rope was formed. However, such a combination can be made to perform successfully in a cooker extruder by derivatizing with a higher percentage of derivatizing reagent thus lowering the gelatinization temperature or by using a lower percentage of the crosslinking reagent.

Pregelatinized starches (i.e., cold-water-dispersible starches), such as pregelatinized converted starches, derivatized starches, and converted and derivatized starches, are also useful herein. They are typically prepared by thermal, chemical, or mechanical gelatinization. The term "gelatinized" or "cooked" starch refers to swollen starch granules which have lost their polarization crosses and which may or may not have lost their granular structure. The thermal processes generally used to prepare such starches include drum-drying, extrusion, and conventional spray-drying.

Drum-drying involves simultaneously cooking and drying a very high viscosity, semi-solid starch paste on heated drums. The dried sheets are scraped off the drum with a metal knife and then ground. This process can be conveniently carried out at a high starch solids content (typically maximum of about 43%).

Extrusion may also be used to simultaneously cook and dry starches (see U.S. Pat. No. 3,137,592 issued June 16, 1964 to T. F. Protzman et al.). This method involves the physical working of a starch-water mixture at elevated temperatures and pressures, causing the gelatinization of the starch, followed by expansion after exiting the die for flashing off the water. The temperature and pressure are generated by mechanical shear between the rotating screw (auger) and cylindrical housing barrel) of the extruder.

Conventional spray-drying may also be used to simultaneously cook and dry the starch. In the typical process, an aqueous slurry of the starch is precooked prior to atomization into a large chamber carrying a stream of hot air. The atomization (i.e., breaking the feed into very fine particles) is accomplished with high pressure single-fluid nozzles, with two-fluid nozzles in which compressed air or steam is the atomizing medium, or with a rapidly rotating centrifugal disc. Spray-drying is usually limited to "thin-cooking starches", i.e., converted starches where the polymeric structure has been degraded by acid or enzyme hydrolysis. Converted starches can be used at higher solids because their pastes are lower in viscosity and can be atomized.

The starches useful in combination with the spray-dried, pregelatinized high amylose starches can be prepared from any starch base. Such bases include corn, potato, sweet potato, rice, sago, tapioca, waxy maize, sorghum, or the like. Starch flours may also be used as a starch source.

The above starch modification procedures, i.e. conversion, derivatization, crosslinking, and pregelatinization are conventional and well-known to those skilled in the art and described in such publications as "Handbook of Water-Soluble Gums and Resins", Robert L. Davidson (Editor), Chapter 22: Starch and Its Modifications by M. W. Rutenberg, McGraw Hill Book Co. (New York) 1980. In the preparation of the modified starches, the derivatization, crosslinking, and/or conversion is typically carried out prior to the pregelatinization step; however, it is possible to pregelatinize the starch prior to these treatments.

Natural or artificial flavorants, natural fruit purees, juice concentrates, acidulants, colorants, fats and/or oils, surfactants, humectants, vitamins, preservatives and other optional ingredients can be added as desired to provide a desired jelly gum confectionary or pharmaceutical product.

The ingredients can be mixed together in a mixing kettle. Preheating the mixture to ensure flowability is necessary when a cooker extruder is used. Precooking (batch cooking) of the ingredients is required when a former extruder is used. The heating is carried out at 93°–149° C. (200°–300° F.) for a cooker extruder and at 93°–116° C. (200°–240° F.) for a former extruder for a time sufficient to disperse the pregelatinized high amylose starch and optional starch. Various commercial mixing units (i.e., steam-jacketed, scraped surface kettles, heated agitators and batch blenders may be employed to heat and disperse the ingredients of the mixture. The advantage of these spray-dried, pregelatinized high amylose starches is that they fully disperse at temperatures as low as 43° C. (110° F.). The mixture is heated at the higher temperature to help solubilize the sweetener and other components. The preheated mixture is poured into the extruder. The extrudate in the form of a rope may be fed onto sugared trays or onto film sheets or may be cut immediately at the die face. The extrudate can be cut with oil or water-lubricated scissors or a knife, either immediately upon extrusion or after some cooling.

Although all the examples utilize a single screw cooker extruder or former extruder, a sophisticated twin screw cooker extruder containing multi-ingredient injection ports may also be used to ensure adequate heating and dispersion of the mixture The selection and/or arrangement of extruders is within the skill of the art.

The orifice may be sized and shaped to provide a desired form to the gel confection. Generally, piece sizes and shapes may be changed by changing the die assembly or, in some cases, by merely changing the die inserts. A variable speed sizing knife at the die permits the control of the extrudate length. Typically, the extrudate benefits from a brief air cooling between the die and the sizing knife—usually for pieces that are to be used as ribbons. If the pieces are to be cut into morsels, the cutting can be carried out as the extrudate leaves the die.

The sweeteners used are those typically employed in the preparation of jelly gum candies. They may include a wide array of sweeteners and sweetening agents, for example, sucrose, dextrose, fructose, corn syrup, high fructose corn syrup, corn syrup solids, invert syrup, and maltodextrins. In general, these sweeteners include all commonly used mono- and disaccharides. Non-nutritive sweeteners, for example, aspartame, saccharin, and the like may also be employed.

The jelly gum confectionaries may also contain various optional confectionary ingredients including, for example, natural flavorants (preferably fruit) and artificial flavorants, coloring agents, fats, oils, surfactants, humectants, vitamins and preservatives.

The natural fruit flavorants may include fruit purees and their concentrates which have a high moisture content, in which case it may not be necessary to use added water in the confectionary mixture. Dehydrated fruit solids may also be used. The dehydrated solids may consist entirely of fruit, preferably the dried fruit solids prepared according to the procedure described in U.S. Pat. No. 3,940,505 (issued Feb. 24, 1976 to B. Nappen et al.) where the fruit is drum-dried in the presence of a suitable amount of a granular or pregelatinized starch.

Under mild processing temperatures there is little danger of affecting the taste and color characteristics of the finished confection. Since a spray-dried, pregelatinized high amylose starch is used in the process, high pressures are not needed to gelatinize the starch. The product will continuously extrude in the form of a rope and can be suitably cut to desired shapes. The extruded confection can be further processed to provide various forms.

In the examples which follow, all parts and percentages are given by weight and all temperatures are in degrees Celsius unless otherwise noted. The amylose content of the starches exemplified are only approximate percentages as values are only reliable within about a 4% range.

The following test procedures were used:

Gel Strength

The gel strength of the jelly gum candy is measured 24 hours after cooling using a Stevens LFRA Texture Analyzer employing probe #5 (0.5 in. cylinder) run at 3 mm./sec. The force (in grams) required to penetrate the candy a distance of 3 mm. with the #5 probe is measured three times and the average of the three measurements recorded.

Water Fluidity

Water fluidity of the starches is measured using a Thomas Rotational Shear-Type Viscometer (manufactured by Arthur H. Thomas Co., Philadelphia, PA.), standardized at 30° C. with a standard oil having a viscosity of 24.73 cps., which oil requires 23.12±0.05 sec. for 100 revolutions. Accurate and reproducible measurements of the water fluidity are obtained by determining the time which elapse for 100 revolutions at different solids levels depending on the starch's degree of treatment (as treatment increases, the viscosity decreases).

The procedure used involves slurrying the required amount of starch (e.g., 11.4 or 13.20 g. on a dry basis) in 100 ml. of distilled water in a covered copper cup and heating the slurry in a boiling water bath for 30 min. with occasional stirring. The starch dispersion is then brought to the final weight (e.g., 113 or 115 g.) with distilled water. The time required for 100 revolutions of the resultant dispersion at 81°–83° C. is recorded and given a water fluidity number as defined in the table below.

Amount of Starch Used
(anhydrous)

| 11.44 g. | 13.20 g. | |
|---|---|---|
| Time required for 100 revolutions (sec.) | | Water Fluidity |
| 32.5 | | 45 |
| 26.5 | | 50 |
| 22.0 | | 55 |
| | 24.2 | 60 |
| | 19.2 | 65 |
| | 15.9 | 70 |
| | 13.5 | 75 |
| | 11.5 | 80 |
| | 10.0 | 85 |
| | 9.0 | 90 |

EXAMPLE I

The unique spray-dried high amylose starches used in the following Examples were prepared by two methods.

Part A—Granular Spray—Dried Hylon VII Starches

The starch was prepared by processing the high amylose starch in a spray-drier fitted with nozzles based on a design shown in U.S. Pat. No. 4,280,851 (cited previously). Three nozzles were fitted at the top of the spray dryer. Each nozzle contained four 0.016 inch orifices (Spraying Systems Inc. orifice #78) and four Spraying Systems #21T flat top cores. Steam was supplied to the nozzles at 180 psi.

A high amylose starch having an amylose content of about 70% (referred to as Hylon VII) was slurried in water at 24.7% solids on a dry basis. The raw starch slurry was pumped under a pressure of 5,000 psi to the atomization nozzles by a Manton-Gaulin high pressure piston pump. Throughput rates averaged 252 pounds of dry starch per hour.

The atomized, steam processed starch was dried in the chamber of a 16 ft diameter Henzey spray dryer and collected as a dry powder. Heated air was supplied to the inlet of the dryer at a temperature of 164°–174° C. (327°–345° F.); the exit temperature was 99° C. (211° F.).

The above starch is designated as spray-dried Hylon VII (granular).

Part B—Granular Spray Dried Hylon V Starches

High amylose starch having an amylose content of about 55% (referred to as Hylon V) was slurried in water at 24.7% solids on a dry basis.

The raw starch slurry was pumped under a pressure of 4,000 to 4,800 psi to the atomization nozzles by a Manton-Gaulin high pressure piston pump. Throughput rates averaged 348 pounds of dry starch per hour. Steam was supplied to the nozzles at 150 psi.

The raw starch slurry was atomized and dried as described above. Inlet temperature of the dryer was 171°–186° C. (340°–367° F.); the exit temperature was 98°–99° C. (209°–210° F.).

The above starch is designated as spray-dried Hylon V (granular).

Part C. Dispersed Spray-Dried Hylon VII Starches

The starches were prepared by continuously jet-cooking the high amylose starch, feeding the cooked starch under elevated temperature and pressure to conventional two fluid spray-drying nozzles, atomizing with steam, and drying to a powder in a conventional spray dryer. This process is referred to as a continuous coupled jet-cooking and spray-drying process.

A high amylose starch (referred to as Hylon VII) was slurried at 16.5% solids on a dry basis in water. This slurry was continuously jet-cooked by direct steam injection in a National Starch and Chemical Corp. Model C-20 jet cooker. The starch slurry flow rate was 3.8 gallons per minute. The cooking temperature was 163° C. (325° F.).

The outlet of the jet cooker was piped directly to a pair of two fluid spray drying atomization nozzles (Spraying Systems Inc., #SU-1J-152-SS) mounted at the top of a 16 ft. diameter Henzey spray dryer. Steam at a pressure of 100 psi was supplied to the nozzles for atomization.

The atomized cooked starch was dried in the chamber of the spray dryer and collected as a dry powder. Heated air was fed to the dryer inlet at 249° C. (480° F.); the exit temperature was 132° C. (270° F.).

The above starch is designated as spray-dried Hylon VII (dispersed).

EXAMPLE II

Jelly gum confectionaries were prepared in a cooker extruder utilizing the following formula:

|  | wt (%) | ss (%) | wt (g.) |
|---|---|---|---|
| High Fructose Corn Syrup (42% fructose) | 30.0 | 22.8 | 3600 |
| Crystalline Fructose | 11.0 | 11.0 | 1320 |
| Spray-dried, Dispersed High Amylose Starch (70% Amylose)* | 4.4 | 4.2 | 528 |
| Modified Tapioca Starch** | 6.6 | 6.3 | 792 |
| Granulated Sucrose (Fine) | 20.0 | 20.0 | 2400 |
| 42 D.E. Coarse Corn Syrup Solids | 16.8 | 16.8 | 2016 |
| Water | 11.2 | — | 1344 |
|  | 100.0 | 81.1 | 12000 |

DE means dextrose equivalent
ss means soluble solids
*Prepared by the procedure of Example I - Part C
**Pregelatinized converted and crosslinked tapioca starch A total of 1320 g. of crystalline fructose was thoroughly dry blended with 528 g. of the spray-dried, dispersed high amylose starch. This dry blend was added to a 91° C. (195° F.) blend of 1800 g. of the high fructose corn syrup and 1344 g. of water with high agitation over a period of 5 minutes. After dissolving the blend in the liquid, the remaining 1800 g. of the high fructose corn syrup was added. A dry blend of the remaining ingredients (the modified tapioca starch, granulated sucrose, and 42 DE corn syrup solids) was blended into the hot mass using a hand held mixing paddle while maintaining the temperature at approximately 93° C. (200° F.). This mix was transferred while hot into a Bonnot 2½in. Cooker Extruder consisting of four zones and equipped with steam heating and water cooling capability. The hot mass was extruded using a screw speed of 50 RPM and the following temperatures: Zone 1 at 82° C. (180° F.), Zone 2 at 121° C. (250° F.), Zone 3 at 121° C. (250° F.), and Zone 4 at 18° C.(65° F.). A clear rope of candy with acceptable handleability emerged. It was cut at the die with a moist pair of scissors. This rope was later cut into 1 cm. cross sections and a gel strength of 250 g. were recorded.

EXAMPLE III

The procedure and formulation of Example II was repeated replacing the pregelatinized modified tapioca starch with a pregelatinized modified (i.e., derivatized and crosslinked) waxy maize starch and a non-pregelatinized modified (i.e., converted) corn starch (65 W.F.). When the modified waxy maize starch was used a clear rope of candy was extruded. It had a lower gel strength (143 g.) than the candy of Example II but still had an acceptable handleability. When the fluidity corn starch was used, no rope was formed. This demonstrates that a non-pregelatinized converted corn starch cannot be used in a cooker extruder.

EXAMPLE IV

To determine the unique properties of the spray dried, dispersed high amylose starch (70% amylose), the procedure and formulation of Example II was repeated several times replacing the high amylose starch with the following starches: modified pregelatinized tapioca starch (acid-converted and crosslinked); cook-up high amylose starch (55% amylose); pregelatinized unmodified corn starch; spray-dried, granular high amylose starch (70% amylose) (prepared as in Example I - Part A); spray-dried granular high amylose starch (55% amylose) (prepared as in Example I - Part B); and spray-dried dispersed high amylose starch (55% amylose) (prepared as in Example I - Part C). The same total starch level (11%) was maintained.

The results are shown in Table I.

TABLE I

|  | Extrudate | | | |
|---|---|---|---|---|
| Starch Used (wt. %) | Rope Formation | Handle-Clarity | Gel Strength | Handleability/ Commercial Feasibility |
| Modified pregelatinized tapioca (11.0) | Poor | Good | Negligible | Unacceptable |
| Cook-up high amylose*/ Modified pregelatinized tapioca (4.4/6.6) | None | Good | None | Unacceptable |
| Unmodified pregelatinized corn Modified pregelatinized tapioca (4.4/6.6) | Fair | Good | Low | Unacceptable** |
| Spray-dried granular high amylose (70% amylose)/Modified pregelatinized tapioca (4.4/6.6) | Good | Slightly Cloudy | High | Acceptable |
| Spray-dried granular high amylose (55% | Good | Good | High | Acceptable |

TABLE I-continued

| Starch Used (wt. %) | Extrudate | | | |
|---|---|---|---|---|
| | Rope Formation | Handle-Clarity | Gel Strength | Handleability/ Commercial Feasibility |
| amylose)/Modified pregelatinized tapioca (4.4/6.6) | | | | |
| Spray-dried dispersed high amylose (55% amylose)/Modified pregelatinized tapioca (4.4/6.6) | Good | Slightly Cloudy | Fair | Acceptable |

*A cook-up high amylose starch was used in the extrusion process of U.S. Pat. No. 3,265,509 (discussed in the Background).
**Set up prematurely in hopper and produced only minimal amounts of extrudate.

EXAMPLE V

All of the starch of the confectionary formulation of Example II was replaced with a spray-dried, dispersed high amylose starch (70% amylose) and spray-dried, granular high amylose starch (55% amylose) to determine the feasibility of using a pregelatinized spray-dried high amylose starch as the sole starch in an extruded confectionary.

The spray-dried, dispersed starch prepared by the continuous jet-cooking process described in Part C of Example I is preferred, with the extrudate forming a good rope with good clarity, acceptable handleability, and high gel strength (907 g.). The spray-dried, granular high amylose starch was satisfactory, with the extrudate forming a fair rope with acceptable handleability and high gel strength (938 g) but with less clarity (cloudy). Both were commercially feasible.

EXAMPLE VI

To determine the lower limit at which the spray-dried, dispersed high amylose starch (70% amylose) imparted functionality to the confectionary gel, the total level of starch in the formulation of Example II was lowered to 7% and 9%. The level of coarse corn syrup solids was subsequently raised to 20.8% and 18.8%, respectively. At 7% no rope formed and the extrudate was opaque. At 9% no rope formed but the extrudate was clear. At 11% a rope formed that had acceptable handleability, good clarity, and a gel strength of 907 g.

The results indicate that for this particular blend a total starch level of greater than 9% is required.

EXAMPLE VII

To examine the ability of the pregelatinized high amylose starches to disperse in a high solids environment, spray-dried, dispersed high amylose starches (70% amylose) were used as the total starch in the formulation of Example II. Instead of adding the crystalline fructose and high amylose starch to the corn syrup and water and heating the mixture prior to the addition of the remaining corn syrup and remaining ingredients, a blend of all the dry ingredients was added to a 91° C. (195° F.) mixture of all of the wet ingredients and blended in with mixing paddle. The hot mass was then extruded using a screw speed of 50 RPM and the following temperatures in each zone: Zone 1 at 82° C. (180° F.), Zone 2 at 121° C. (250° F.), Zone 3 at 149° C. (300° F.), and Zone 4 at 18° C. (65° F.).

The rope formation and clarity were good; the handleability and gel strength (164 g.) were acceptable. The results show that the premixing procedure of Example II can be simplified.

EXAMPLE VIII

To define the lower ratio of the preferred spray-dried, dispersed high amylose starch (70% amylose) to pregelatinized starch, the amount of high amylose starch in the blend was reduced from 40% to 15% and amount of modified tapioca starch in the blend was increased from 60% to 85%.

When the blend was used in the formulation of Example II at a total starch level of 15%, the mix was very viscous and set up prematurely. No rope formed and the extrudate had poor clarity and very poor handleability. When the blend was used in the formulation at a total starch level of 12%, a good rope formed. The clarity, and gel strength (421 g.) were good. The amount of 42 D.E. corn syrup solids in the confectionary formulation of Example II was decreased to adjust for the increase in total starch solids from 11% to 15%).

This means that at 12% total starch only about 2 parts out of a total of 10 parts of the pregelatinized high amylose starch is required.

EXAMPLE IX

Various starches and starch levels were evaluated in the confectionary formulation of Example II as shown in Table II:

TABLE II

| Starch Used wt. (%) | Extrudate | | | |
|---|---|---|---|---|
| | Rope Formation | Clarity | Gel Strength* | Handleability Commercial Feasibility |
| Unmodified corn/ Pregelatinized modified tapioca (comparative) (4.4/6.6) | good | good | 96.1 | Unacceptable |
| Cold-water-soluble corn** (room temperature prep) (comparative) (11) | poor | poor | 560.4 | Unacceptable |
| Cold-water-soluble corn | none | good | *** | Unacceptable |

TABLE II-continued

| | Extrudate | | | |
|---|---|---|---|---|
| Starch Used wt. (%) | Rope Formation | Clarity | Gel Strength* | Handleability Commercial Feasibility |
| (heat prep) (comparative) (11) | | | | |
| Spray-dried, dispersed high amylose (70% amylose)/ Non-pregelatinized, highly stabilized, lightly crosslinked waxy maize (comparative) (5.2/7.8) | none | good | *** | Unacceptable |
| Spray-dried, dispersed high amylose (70% amylose)/ Pregelatinized modified tapioca (comparative) (2.25/12.75) | none | poor | *** | Unacceptable |
| Spray-dried, dispersed high amylose (70% amylose)/ Non-pregelatinized, highly stabilized, lightly crosslinked waxy maize (comparative) (7.8/5.2) | poor | good | *** | Unacceptable |

*Gel strength measurements were taken after 24 hours cooling; the gel strength at the time the rope exits the die is more important than that developed on cooling and is reported as handleability. Thus, an extrudate can have a high 24 hour gel strength and yet be unacceptable.
**This starch is described in U.S. Pat. No. 4,567,055 (to C.O Moore). The room temperature preparation is the preferred procedure of the Moore patent.

EXAMPLE X

This example compares the use of a dry blend (40/60) of a spray-dried dispersed high amylose starch (70% amylose) and the modified tapioca starch described in Example II with the use of a spray-dried dispersed blend (40/60) of a high amylose starch (70% amylose) and an acid-converted corn starch (40 W.F.) coprocessed using the coupled jet-cooking/spray drying process.

The confectionary formulation was as follows:

| | Weight (%) | Soluble Solids (%) |
|---|---|---|
| 62 D.E. Corn Syrup | 41.4 | 33.8 |
| Sugar | 28.2 | 28.2 |
| Starch | 9.5 | 9.0 |
| Water | 20.9 | — |
| | 100.0 | 71.0 |

It was prepared by adding the starch to the corn syrup, thoroughly blending, adding water, and mixing. The slurry temperature was raised to a boil and the sugar was added with mixing. The mixture was boiled until the finished solids were 82%.

It was extruded using the zone temperature conditions used in Example II.

The extrudates had the following properties:

| Starch | Rope Formation | Clarity | Gel Strength | Commercial Feasibility |
|---|---|---|---|---|
| Dry Blend | Good | Excellent | Medium | Acceptable |
| Coprocessed | Good | Good | High | Acceptable |

This shows that a coprocessed starch blend will yield an acceptable extruded product (i.e., a commercially feasible product).

EXAMPLE XI (comparative)

A confectionary formulation containing a 50/50 blend of the spray dried high amylose starches of Example I and a granular converted corn starch (65 W.F.) was extruded using Kitchen Aid Food Grinder Extruder/(Model No. K5SS) (a laboratory scale type of former extruder). For comparison the cold-water-soluble, granular ethanol-extracted corn starch of U.S. Pat. No. 4,567,055 was also evaluated The ropes were extruded onto a bed of sugar.

The confectionary formulation continued:

| | % | % ss | g. |
|---|---|---|---|
| 62 DE Corn Syrup* | 30.00 | 24.5 | 360 |
| Sugar | 19.00 | 19.0 | 228 |
| Spray-dried High Amylose Starch | 3.25 | 2.9 | 39 (anhydrous) |
| 65 W.F. Corn Starch | 3.25 | 2.9 | 39 (anhydrous) |
| Water | 44.5 | — | 534 |
| | 100.00 | 49.3 | 1200 |

The starches were separately dry blended 1:1 with the sugar. The blend of the 65 W.F. Corn Starch and sugar was added with stirring to the heated corn syrup. The blend of the spray-dried high amylose starch and sugar was added to water at 212° F. (100° C.) with agitation, heated for 30 seconds after the addition was complete, and cooked for 10 minutes. The heated corn syrup mixture was then added to the aqueous mixture. The mixture was then boiled down to 83% solids.

The confectionary formulations containing the dispersed spray-dried Hylon VII starch spray-dried using the continuous coupled jet cooking/spray drying process and the granular Hylon VII starch spray-dried using the process of U.S. Pat No. 4,280,851 made an extrudable rope, which was slightly sticky but which dried and hardened to a firm but pliable texture. The texture was unchanged after two weeks storage (i.e., it had not become rock hard). The rope prepared with the spray-dried granular Hylon V starch was slightly softer than those prepared with the Hylon VII starch.

The confectionary formulation containing the cold-water-soluble corn starch was so sticky and cohesive that it could not be put through the food grinder extruder.

EXAMPLE XII

This example describes confectionary formulations suitable for use in a former extruder.

Part A

The confectionary formulation consists of:

|  | Weight (%) | Soluble Solids (%) |
|---|---|---|
| 62 D.E. Corn Syrup | 18.3 | 14.9 |
| High Fructose Corn Syrup (42%) | 9.9 | 7.0 |
| Sugar (granulated) | 21.1 | 21.0 |
| Starch* | 7.7 | 7.0 |
| Water | 43.0 | — |
|  | 100.0 | 50.0 |

The starch used is a 40/60 blend of the spray-dried dispersed high amloyse starch (70% amylose) and a granular converted corn starch (40 W.F.).

The 62 D.E. corn syrup and high fructose corn syrup are mixed. The starch is then added with thorough mixing, followed by all of the water. The slurry is boiled for 10 min. while mixing. The sugar is then added and the mixture is boiled until the soluble solids are 82%. Colorant, flavorant, and acid are added as desired. The mixture is then processed through a former extruder.

Part B

The confectionary formulation consists of:

|  | Weight (%) | Soluble Solids (%) |
|---|---|---|
| 62 D.E. Corn Syrup | 21.9 | 17.9 |
| High Fructose Corn Syrup (42%) | 9.7 | 9.7 |
| Sugar (granulated) | 17.7 | 17.7 |
| Starch* | 10.2 | 9.7 |
| Corn Syrup Solids | 16.0 | 16.0 |
| Water | 24.5 | — |
|  | 100.0 | 71.0 |

*The starch used is a 40/60 blend of the spray-dried dispersed high amloyse starch (70% amylose) and a pregelatinized modified tapioca starch.

The formulation was prepared by adding all the sugar to 7 parts of the water and mixing thoroughly, adding the starch and mixing thoroughly, and adding the remaining water while stirring the mixture. The slurry is brought to a boil. The corn syrup solids and fructose are added with mixing. The mixture is boiled until the soluble solids are 82%. Colorant, flavorant and acids are added as desired. The mixture is processed through a former extruder.

EXAMPLE XIII

This example describes the use of a starch blend containing the dispersed high amylose starch in an extruded pharmaceutical product. The formulation is as follows:

|  | wt % | % ss |
|---|---|---|
| 62 DE Corn Syrup | 20.0 | 16.3 |
| Fructose | 15.0 | 15.0 |
| Sucrose | 18.4 | 18.4 |
| Spray-dried Dispersed High Amylose Starch* (70% amylose) | 5.8 | 5.6 |
| Modified Tapioca Starch** | 8.7 | 8.4 |
| 42 DE Corn Syrup Solids | 18.1 | 18.1 |
| Menthol/Eucalyptus Oil (1:2) | 0.6 | 0.6 |
| Water | 13.4 | — |
| (Flavor), color, acid to suit. | 100.0 | 81.5 |

*Prepared as in Example I - Part C.
**Acid-converted with hydrochloric acid and crosslinked with sodium trimetaphosphate.

The formulation is prepared by mixing the fructose and sucrose into room temperature water, adding the starch blend, and thoroughly mixing. The slurry is brought to a boil and the remainder of ingredients are added and mixed thoroughly while maintaining the temperature of the slurry at 93° C. (200° F.). The mixture is then fed into a Bonnot 2¼ in. cooker extruder. The 1st zone is maintained at 93° C. (200° F.), the 2nd at 149° C. (300° F.), the 3rd at 135° C. (275° F.), and the 4th at 18° C. (65° F.). The extrudate is cut at the die, air-dried for 24 hours, polished, and packaged.

Now that the preferred embodiments of the invention have been described in detail, various modifications and improvements thereon will became readily apparent to those skilled in the art. Accordingly, the spirit and scope of the present invention are to be limited only by the appended claims and not by the foregoing specification.

What is claimed is:

1. A process for the manufacture of a gelled product in a cooker extruder comprising the steps of:
   (a) mixing about 10 to 18%, on dry solids basis, of a spray-dried, pregelatinized high amylose starch having an amylose content of at least about 40% amylose, about 70 to 90% of a sweetener, and water present in a total amount of 0 to about 20%, the percentages being by weight and totaling 100%; wherein the spray-dried, pregelatinized high amylose starch comprises (i) an uniformly gelatinized granular starch in the form of indented spheres, with at least a majority of the granules being whole and unbroken, the starch granules being in the form of loosely-bound agglomerates or individual granules, (ii) a fully dispersed, non-granular starch which is substantially non-crystalline and substantially non-retrograded, and (iii) mixtures thereof;
   (b) heating the mixture to about 93° C. (200° F.) to provide a flowable mixture;
   (c) introducing the hot mixture into a cooker extruder and heating at about 93°–149° C. (200°–300° F.) for a time sufficient to fully disperse the starch; and
   (d) extruding the mixture as a firm gel.

2. A process for the manufacture of a gelled product in a former extruder comprising the steps of:
   (a) mixing about 10 to 18%, on dry solids basis, of a spray-dried pregelatinized high amylose starch having an amylose content of at least about 40% amylose, about 70 to 90% of a sweetener, and water present in a total amount of 0 to about 20%, the percentages being by weight and totaling 100%; wherein the spray-dried, pregelatinized high amylose starch comprises (i) an uniformly gelatinized granular starch in the form of indented spheres, with at least a majority of the granules being whole and unbroken, the starch granules being in the form of loosely-bound agglomerates or individual granules, (ii) a fully dispersed, non-granular starch which is substantially non-crystalline and substantially non-retrograded, and (iii) mixtures thereof;

(b) heating the mixture to about 93°–116° C. (200°–240° F.) for a time sufficient to fully solubilize the sugar and the starch and to increase the solids to about 80 to 86% solids;

(c) introducing the hot mixture into a former extruder; and (d) extruding the mixture as a firm gel.

3. The process of claim 1 or claim 2, wherein the gelled product is a jelly gum confectionary and wherein the mixture of step (a) also contains up to about 20% of a confectionary ingredient selected from the group consisting of a flavorant, colorant, fat, oil, surfactant, humectant, vitamin, preservative and mixtures thereof, and wherein the starch is present in an amount of about 11%.

4. The process of claim 1 or 2, wherein the gelled product is a jelly gum confectionary and wherein the mixture of step (a) also contains up to about 20% of a confectionary ingredient selected from the group consisting of a flavorant, colorant, fat, oil, surfactant, humectant, vitamins, preservative and mixtures thereof and wherein the starch blend is present in an amount of about 11%.

5. The process of claim 4, wherein the starch blend comprises the spray-dried, pregelatinized high amylose starch and an acid-converted, crosslinked tapioca starch or a granular converted corn starch and wherein the spray-dried pregelatinized high amylose starch is an unmodified starch.

6. The process of claim 5, wherein the starch blend is a 40:60 to 60:40 blend of the unmodified spray-dried, pregelatinized high amylose starch and wherein the unmodified high amylose starch has an amylose content of about 55 to 70%.

7. The process of claim 1 or 2, wherein the sweetener is sucrose, fructose, dextrose, corn syrup solids, corn syrup, high fructose corn syrup or mixtures thereof.

8. The process of claim 7, wherein the corn syrup is present 8in an amount of about 41% and the sucrose is present in an amount of about 28% and wherein the high fructose corn syrup is present in an amount of about 30% and the sucrose, fructose, and corn syrup solids are present in an amount of about 48%.

9. The process of claim 1, wherein in step (a) the mixture consists essentially of the spray-dried, pregelatinized high amylose starch in a blend with an acid-converted, crosslinked tapioca starch, with the starch blend being about 11%, about 30% high fructose corn syrup having a 42% concentration of fructose, about 20% granulated sucrose, about 11% crystalline fructose, about 16.8% coarse corn syrup solids having a dextrose equivalent of 42 and the remainder water, wherein the starch blend is a 40:60 blend of the high amylose starch and the tapioca starch and wherein the high amylose starch has an amylose content of about 50 to 70%.

10. The extruded confection of claim 3.

11. The extruded confection of claim 4.

12. The process of claim 1 or claim 2, wherein the spray-dried, pregelatinized high amylose starch is present in a blend with up to about 8 parts out of a total of 10 parts of a modified starch selected from the group consisting of a derivatized starch, a pregelatinized starch other than a high amylose starch, and mixtures thereof.

13. The process of claim 1 or claim 2, wherein the spray-dried, pregelatinized high amylose starch is an unmodified starch.

14. The process of claim 12, wherein the spray-dried pregelatinized high amylose starch is an unmodified starch.

15. The process of claim 1 or claim 2, wherein the spray-dried, pregelatinized high amylose starch is a modified starch.

16. The process of claim 12, wherein the spray-dried, pregelatinized high amylose starch is a modified starch.

17. The process of claim 12, wherein the sweetener is sucrose, fructose, dextrose, corn syrup solids, corn syrup, high fructose corn syrup or mixtures thereof.

18. The process of claim 17, wherein the corn syrup is present in an amount of about 41% and the sucrose is present in an amount of about 30% and the sucrose, fructose, and corn syrup solids are present in an amount of about 48%.

19. The extruded confection of claim 5.

20. The extruded confection of claim 6.

* * * * *